(12) United States Patent
Lombardo et al.

(10) Patent No.: US 8,075,602 B2
(45) Date of Patent: Dec. 13, 2011

(54) BONE PLATE ASSEMBLY PROVIDED WITH SCREW LOCKING MECHANISMS

(75) Inventors: Alan Lombardo, Kinnelon, NJ (US); David Edgar Evans, Downingtown, PA (US)

(73) Assignee: Blackstone Medical, Inc., Springfield, MA (US)

( * ) Notice: Subject to any disclaimer, the term of this patent is extended or adjusted under 35 U.S.C. 154(b) by 0 days.

(21) Appl. No.: 11/901,006

(22) Filed: Sep. 14, 2007

(65) Prior Publication Data

US 2008/0009870 A1    Jan. 10, 2008

Related U.S. Application Data

(63) Continuation of application No. 10/676,062, filed on Oct. 1, 2003, now Pat. No. 7,273,481.

(60) Provisional application No. 60/421,819, filed on Oct. 28, 2002.

(51) Int. Cl.
*A61B 17/80* (2006.01)

(52) U.S. Cl. ........ 606/290; 606/280; 606/286; 606/289; 606/291

(58) Field of Classification Search .......... 606/280–299, 606/70–71, 902–906, 915, 86 A, 86 B, 268, 606/269; 74/17; 411/11, 136, 313, 368, 411/371.2, 533, 148, 160–171, 272–273
See application file for complete search history.

(56) References Cited

U.S. PATENT DOCUMENTS

| | | | |
|---|---|---|---|
| 1,756,239 A | 6/1930 | Muerling | |
| 2,401,856 A | 6/1946 | Brock | |
| 3,534,731 A | 10/1970 | Muller | |
| 3,695,259 A | 10/1972 | Yost | |
| 3,741,205 A | 6/1973 | Markolf et al. | |
| 4,794,918 A | 1/1989 | Wolter | |
| 5,057,111 A | 10/1991 | Park | |
| 5,073,070 A * | 12/1991 | Chang | 411/353 |
| 5,147,361 A | 9/1992 | Ojima et al. | |
| 5,234,431 A | 8/1993 | Keller et al. | |
| 5,261,910 A | 11/1993 | Warden et al. | |
| 5,269,784 A | 12/1993 | Mast | |
| 5,330,535 A | 7/1994 | Moser et al. | |
| 5,344,421 A | 9/1994 | Crook | |
| 5,364,399 A | 11/1994 | Lowery et al. | |
| 5,486,176 A | 1/1996 | Hildebrand et al. | |
| 5,534,027 A | 7/1996 | Hodorek | |
| 5,549,612 A | 8/1996 | Yapp et al. | |
| 5,578,034 A | 11/1996 | Estes | |
| 5,601,553 A | 2/1997 | Trebing et al. | |
| 5,616,144 A * | 4/1997 | Yapp et al. | 606/280 |

(Continued)

FOREIGN PATENT DOCUMENTS

EP    0 502 815    5/1992

(Continued)

*Primary Examiner* — Thomas C. Barrett
*Assistant Examiner* — Michael T Schaper
(74) *Attorney, Agent, or Firm* — Baker & McKenzie LLP

(57) ABSTRACT

One embodiment of the present invention is directed to a bone plate assembly that includes a bone plate, bone screw(s) received in aperture(s) in the bone plate, and screw fixation member(s). The screw fixation member(s) may, alone or in conjunction with the bone plate, fix the bone screw(s) in place when such bone screw(s) are inserted in the aperture(s) in the bone plate. In one example (which example is intended to be illustrative and not restrictive) when the bone screw(s) have been received by the bone plate and inserted into bone and/or tissue, the bone plate assembly can be used to fuse anatomical structures together (such as adjoining bones) and/or to heal a fracture in bone.

38 Claims, 18 Drawing Sheets

U.S. PATENT DOCUMENTS

| | | | | |
|---|---|---|---|---|
| 5,681,311 A | | 10/1997 | Foley et al. | |
| 5,735,853 A | * | 4/1998 | Olerud | 606/71 |
| 5,741,258 A | | 4/1998 | Klaue et al. | |
| 5,876,402 A | * | 3/1999 | Errico et al. | 606/287 |
| 5,904,683 A | | 5/1999 | Pohndorf et al. | |
| 5,951,558 A | | 9/1999 | Fiz | |
| 5,954,722 A | | 9/1999 | Bono | |
| 5,964,762 A | | 10/1999 | Biedermann et al. | |
| 6,017,345 A | | 1/2000 | Richelsoph | |
| 6,106,557 A | | 8/2000 | Robioneck et al. | |
| 6,129,730 A | | 10/2000 | Bono et al. | |
| 6,139,550 A | | 10/2000 | Michelson | |
| 6,152,927 A | * | 11/2000 | Farris et al. | 606/287 |
| 6,159,213 A | | 12/2000 | Rogozinski | |
| 6,193,720 B1 | | 2/2001 | Yuan et al. | |
| 6,193,721 B1 | | 2/2001 | Michelson | |
| 6,206,881 B1 | | 3/2001 | Frigg et al. | |
| 6,206,882 B1 | | 3/2001 | Cohen | |
| 6,224,602 B1 | | 5/2001 | Hayes | |
| 6,228,085 B1 | | 5/2001 | Theken et al. | |
| 6,235,033 B1 | | 5/2001 | Brace et al. | |
| 6,235,034 B1 | | 5/2001 | Bray | |
| 6,241,731 B1 | | 6/2001 | Fiz | |
| 6,258,089 B1 | | 7/2001 | Campbell et al. | |
| 6,261,291 B1 | | 7/2001 | Talaber et al. | |
| 6,273,889 B1 | | 8/2001 | Richelsoph | |
| 6,290,703 B1 | | 9/2001 | Ganem | |
| 6,364,880 B1 | | 4/2002 | Michelson | |
| 6,413,259 B1 | | 7/2002 | Lyons et al. | |
| 6,428,542 B1 | * | 8/2002 | Michelson | 606/70 |
| 6,599,290 B2 | * | 7/2003 | Bailey et al. | 606/86 B |
| 6,602,255 B1 | * | 8/2003 | Campbell et al. | 606/290 |
| 6,613,053 B1 | | 9/2003 | Collins et al. | |
| 6,626,907 B2 | * | 9/2003 | Campbell et al. | 606/86 B |
| 6,692,503 B2 | * | 2/2004 | Foley et al. | 606/96 |
| 6,695,846 B2 | * | 2/2004 | Richelsoph et al. | 606/71 |
| 6,730,091 B1 | * | 5/2004 | Pfefferle et al. | 606/70 |
| 6,964,664 B2 | * | 11/2005 | Freid et al. | 606/281 |
| 7,001,389 B1 | * | 2/2006 | Navarro et al. | 606/71 |
| 7,048,739 B2 | * | 5/2006 | Konieczynski et al. | 606/288 |
| 7,094,239 B1 | * | 8/2006 | Michelson | 606/70 |
| 7,137,984 B2 | * | 11/2006 | Michelson | 606/279 |
| 7,524,325 B2 | * | 4/2009 | Khalili | 606/290 |
| 2002/0151899 A1 | | 10/2002 | Baily et al. | |

FOREIGN PATENT DOCUMENTS

| | | |
|---|---|---|
| EP | 1 169 971 | 1/2002 |
| WO | WO 01/49191 | 7/2001 |

* cited by examiner

BONE PLATE ASSEMBLY PROVIDED WITH SCREW LOCKING MECHANISMS

CROSS-REFERENCE TO RELATED APPLICATIONS

This application is a continuation application of U.S. Ser. No. 10/676,062, filed Oct. 1, 2003, now U.S. Pat. No. 7,273,481, which claims the benefit of U.S. Provisional Application Ser. No. 60/421,819, filed on Oct. 28, 2002, both of which are incorporated herein by reference in their entireties.

FIELD OF THE INVENTION

One embodiment of the present invention is directed to a bone plate assembly that includes a bone plate, bone screw(s) received in aperture(s) in the bone plate, and screw fixation member(s). The screw fixation member(s) may, alone or in conjunction with the bone plate, fix the bone screw(s) in place when such bone screw(s) are inserted in the aperture(s) in the bone plate. In one example (which example is intended to be illustrative and not restrictive) when the bone screw(s) have been received by the bone plate and inserted into bone and/or tissue, the bone plate assembly can be used to fuse anatomical structures together (such as adjoining bones) and/or to heal a fracture in bone.

BACKGROUND OF THE INVENTION

Bone plate assemblies are employed in order to fuse bones or to repair fractures in bones. For example, U.S. Pat. No. 6,413,259, incorporated herein by reference, discloses embodiments for bone plates.

SUMMARY OF THE INVENTION

In one embodiment, the present invention is directed to an arrangement for fixing, in a vertebrate, a screw inserted through a plate. In one example (which example is intended to be illustrative and not restrictive) a bone plate assembly according to the present invention may have at least two bone screws, each received in at least two apertures in the bone plate. The bone plate assembly may also have screw fixation members provided for the bone screws. When the bone screws are inserted through the apertures in the bone plate, and installed in bone and/or tissue at a preselected angle, the presence of the screw fixation members may aid in fixing the bone screws in place. Each bone screw may have a head, sized so that the head does not pass through the bone plate, and a shank provided with threads (e.g., which threads may extend substantially to the tip of the bone screw). In yet another embodiment, the bone plate assembly may be provided with washers (e.g., for each screw employed in the assembly) that reside in the apertures in the bone plate. In yet another embodiment, each washer may be provided with an aperture in which the bone screw is received, when the bone screw is inserted into the bone plate. In yet another embodiment, after the bone screw is received in the aperture in the washer, and inserted in bone and/or tissue, the washer may be actuated to fix the angle at which the bone screw has been inserted (e.g., relative to the bone plate).

In a further embodiment, the washer may be provided with a sidewall, which sidewall defines the aperture though which the bone screw extends. The sidewall may have a thickness that varies with respect to the position along the washer's perimeter. In one embodiment, the washer may be provided with a first sidewall region on its perimeter that is relatively thicker than a second sidewall region.

In yet another embodiment, one or more apertures of the bone plate may be provided with a recess that is cut into the sidewall that defines the aperture in the bone plate. The depth to which the recess is cut may vary around the perimeter of the recess. In yet another embodiment, a first region of the recess may have a depth that is greater than a second region of the recess. In yet another embodiment, a washer may reside partially or fully within the recess.

In yet another embodiment, the washer may reside in the recess, aligned so that the first relatively thicker sidewall region of the washer is positioned within the first relatively deeper region of the recess, and the second relatively thinner sidewall region of the washer is positioned in the second relatively shallower region of the recess. After the bone screw is received in the aperture in the washer, and inserted in bone and/or tissue, the washer may be actuated to fix the angle at which the bone screw has been inserted (e.g., relative to the bone plate). The bone screw may be fixed by rotating the washer, thereby moving the first relatively thicker sidewall region of the washer into the second relatively shallower region of the recess, which effectively causes the first relatively thicker sidewall region to extend laterally, into the aperture in the bone plate, where the washer impinges against the bone screw (e.g., the head of the bone screw), applying a force thereto which wedges the bone screw between the washer and the opposite sidewall of the aperture. This operation thus fixes the bone screw in place, retaining it at a particular angle (e.g., the at which the bone screw is inserted).

In yet another embodiment, the present invention may allow for the bone screw(s) to toggle (i.e., move within a confined range) after being installed through the bone plate and being held by the washer. This can be arranged, for example, by actuating the washer to an intermediate position, which allows the screw to toggle.

In yet a further embodiment of the present invention, a bone plate assembly may be provided in which the bone plate assembly may include a bone plate, bone screw(s) received in aperture(s) in the bone plate, and washer(s). The washer(s) may, alone or in conjunction with the bone plate, fix the bone screw(s) in place when the bone screw(s) are inserted in the aperture(s) in the bone plate. Here the washer of the bone plate assembly may be adapted to reside over the bone screw and be joined therewith in a locking arrangement. In yet another embodiment, the head of the bone screw may be provided with a number of tangs, spaced apart from each other, mounted on the upper surface of the head. The tangs may be mounted upon wedges, which wedges extend up from the head of the screw. The wedges may be not as wide as the tangs, and may be narrowed by an undercut.

In a further embodiment, the washer may be provided with a washer body through which a central opening is provided. A number of lobes may be provided on the periphery of the central opening. In one example (which example is intended to be illustrative and not restrictive) three lobes are provided (it should be understood that other arrangements are, of course, possible). In yet another embodiment, the washer may also be provided with splays which are provided on the exterior of the washer. The splays may be separated from the remainder of the washer body by tracks, which tracks extend into the washer body.

In yet another embodiment, the washer and the wedges and/or tangs may be designed to engage with each other in a locking arrangement. Relative to each other, the wedges may be slightly wider than the width of at least a portion of the track.

In yet another embodiment, when the bone plate assembly is implanted in a person, the bone plate may be positioned on the bone, tissue and bone, or tissue to be joined by the bone plate. The bone screw may be inserted through the aperture in the bone plate and installed in bone and/or tissue by known techniques. The bone screw may be installed at a preselected angle, relative to the bone plate. To fix the screw at the angle at which it is installed, the washer may be placed over the head of the bone screw, and positioned so that the wedges are poised to enter the track portions. In yet another embodiment of the invention, a tool may be provided, the tool having a head adapted to fit within the central washer opening, which tool then engages with the central washer opening, to rotate the washer. The wedges may thereby enter the track portions. Since the wedges maybe wider than at least a portion of the tracks, the splays may be forced outward when the wedges enter the intermediate track portion(s). In this arrangement, the splays may be forced into an abutting arrangement with the sidewalls of the aperture in which the bone screw and washer reside. The abutting arrangement between the splays and the sidewalls of the aperture may fix the bone screw at a particular angle (e.g., the angle at which the bone screw was installed).

In yet another embodiment, a bone plate assembly may be generally provided with a bone plate, at least two bone screws received in apertures in the bone plate, and moveable doors that fix the bone screws in place when the bone screws are inserted in the apertures in the bone plate. The bone screw employed in this embodiment may have a head sized so that the head does not pass through the bone plate. The bone screw may further have a shank provided with threads (e.g., which threads may that extend to the tip of the bone screw). In another embodiment, the bone plate assembly may be provided with a cut out portion on its upper surface, to which the doors are slidably mounted. The cut out portion may be positioned adjacent the bone screw apertures, at a portion of the edge thereof.

In yet another embodiment, the sliding doors may be dimensioned to substantially not cover the apertures in the bone plate in a first position (in which first position the bone screws may be installed), yet slide and at least partially cover the apertures once the screws have been inserted (to thereby fix the bone screws in place). In yet another embodiment, the doors may be positioned in the cut out portion on the upper surface of the bone plate, and may be retained therein by a lip provided at the upper sidewall of the cut out portion. In yet another embodiment, the cut out portion may be sized slightly greater than the sliding doors. Thus, when a bone screw is positioned in the aperture of the bone plate, the sliding door can be slid in the direction of the hole, in order to cover the bone screw (and to fix the bone screw in place).

In yet another embodiment, a bone screw may be provided with a number of splays positioned around the periphery of the head of the bone screw. The splays may be mounted upon wedges that extend up from the head of the screw. In one embodiment, there is a space between at least a portion of the splay and the head of the bone screw. When the screw is installed in an aperture in the bone plate at a preselected angle, a tool may be employed to force the splays outward, into a locking and abutting arrangement with the sidewalls of the bone plate aperture in yet another embodiment, a cam may be positioned in the interior space defined by the splays. When the cam is rotated, the cam may force the splays outward, into a locking and abutting arrangement with the sidewalls of the bone plate aperture. The presence of the cam may further provide a counterforce, which counterforce may maintain the splays in the locking and abutting arrangement.

Among those benefits and improvements that have been disclosed, other objects and advantages of this invention will become apparent from the following description taken in conjunction with the accompanying figures. The figures constitute a part of this specification and include illustrative embodiments of the present invention and illustrate various objects and features thereof.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

Figure 1:
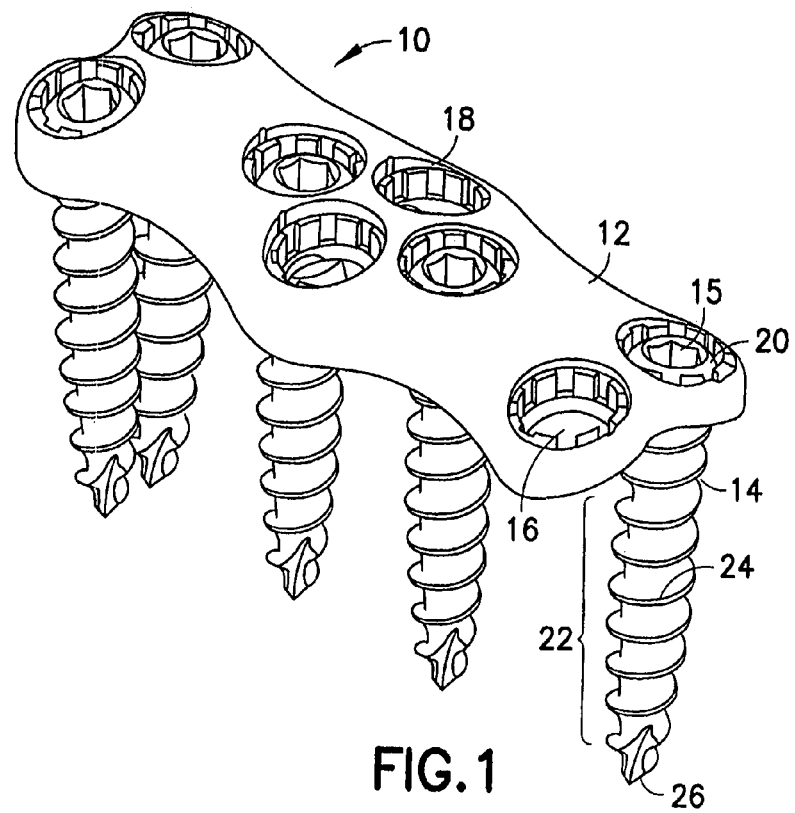
FIG. 1 is a perspective view of an embodiment of the present invention.
Figure 2:
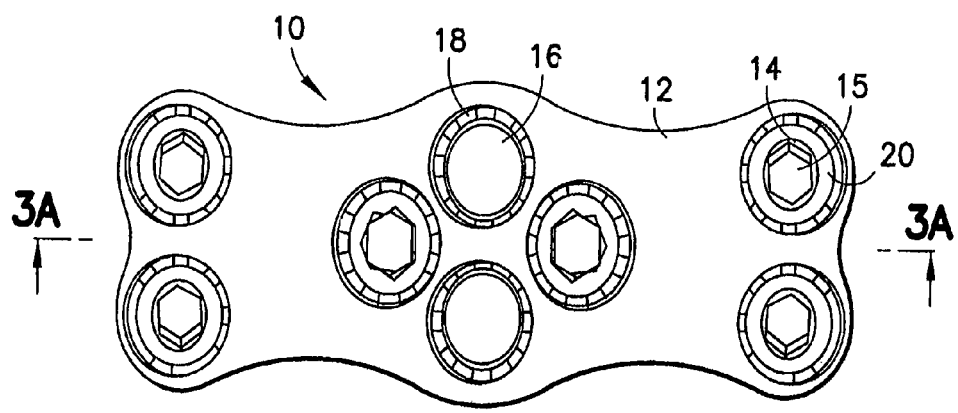
FIG. 2 is a top plan view of the embodiment of FIG. 1.
Figure 3A:
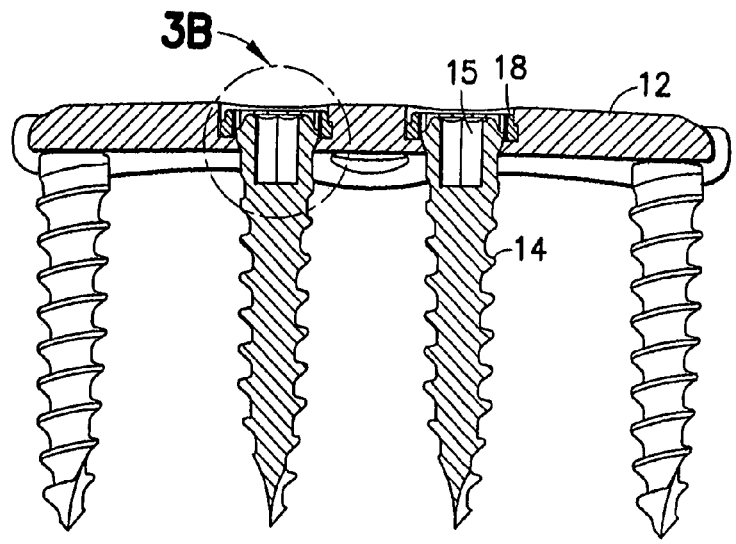
FIG. 3A is a cross sectional view of the embodiment of FIG. 1.
Figure 3B:
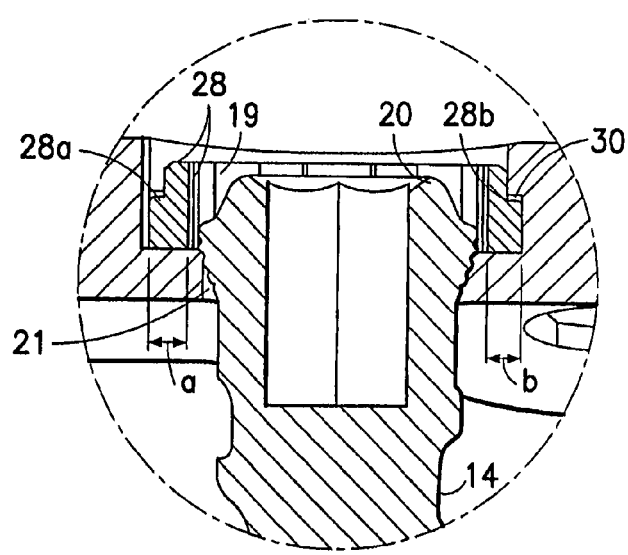
FIG. 3B is a cross sectional view showing in greater detail the circled portion of FIG. 3A.
Figure 4A:
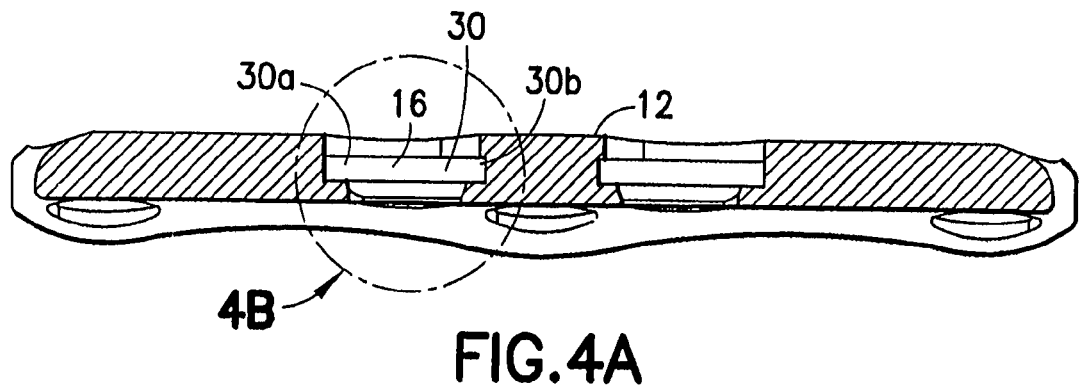
FIG. 4A is a cross sectional view of the bone plate of the embodiment of FIG. 1 (shown across the long side)
Figure 4B:
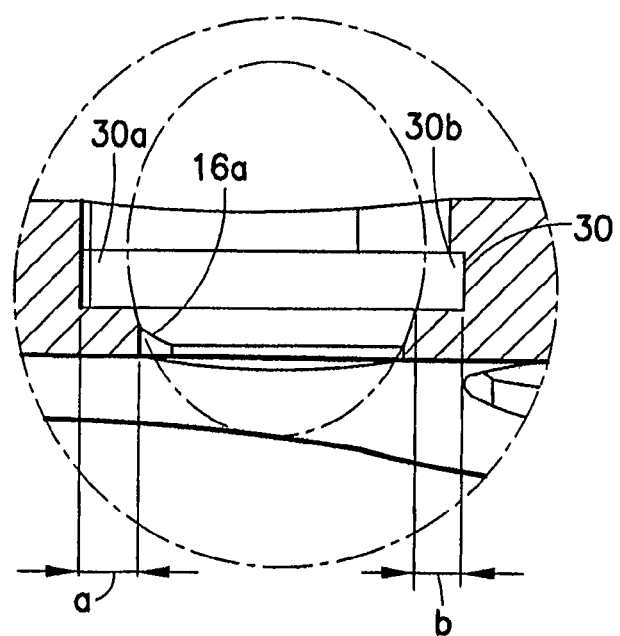
FIG. 4B is a cross sectional view showing in greater detail the circled portion of FIG. 4A.
Figure 5:
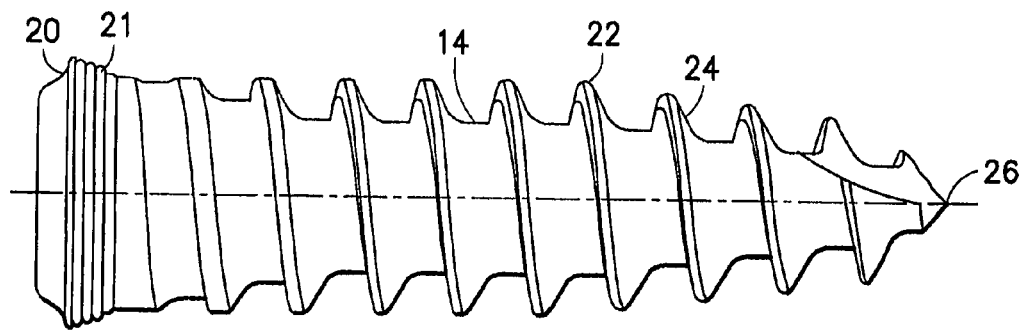
FIG. 5 is a side elevational view of a screw employed in the embodiment of FIG. 1.

Referring now generally to FIGS. 1-3, it is seen that a bone plate assembly 10 is provided with bone plate 12, bone screw(s) 14 received in aperture(s) 16 in the bone plate 12, and washer(s) 18 that, alone or in conjunction with the bone plate 12, fix the bone screw(s) 14 in place (e.g., when the bone screw(s) 14 are inserted in the aperture(s) 16 in the bone plate). Each bone screw 14 has a head 20 sized so that it does not pass through the bone plate 12. Further, each bone screw 14 has a shank 22 provided with threads 24 (e.g., which threads 24 may extend to tip 26). The head 20 of bone screw 14 is further provided with an opening 15 that is dimensioned to mate with the head of a tool, so that the bone screw 14 can be installed in tissue and/or bone. In one embodiment, the head 20 of the bone screw 14 may be provided with grooves 21 (see, e.g., FIGS. 3B and 5). Bone plate assembly 10 is also provided with washer(s) 18. Each washer 18 has an opening 19 though which a bone screw is received (see, e.g., FIG. 3B).

Figure 7A:
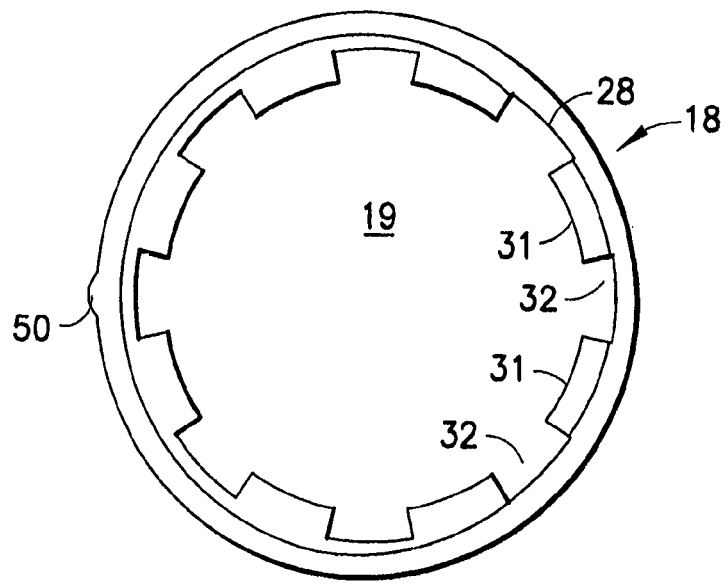
FIG. 7A is a top plan view of a washer used in an embodiment of the present invention.
Figure 7B:
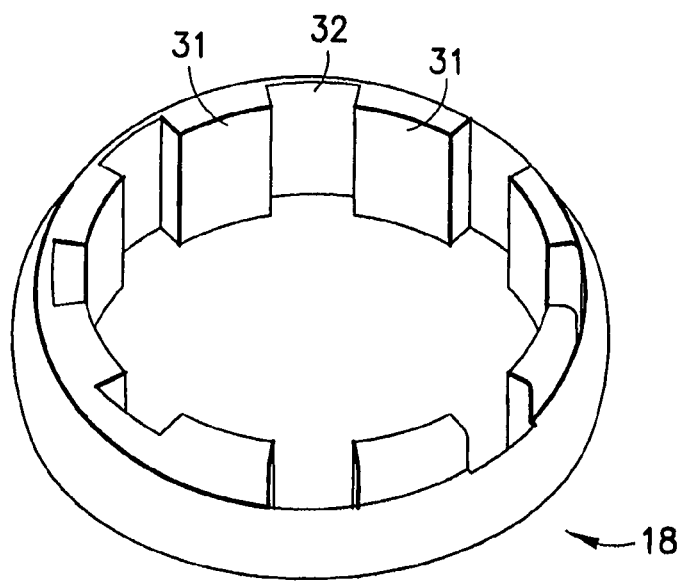
FIG. 7B is a perspective view of the washer of FIG. 7A.
Figure 8A:
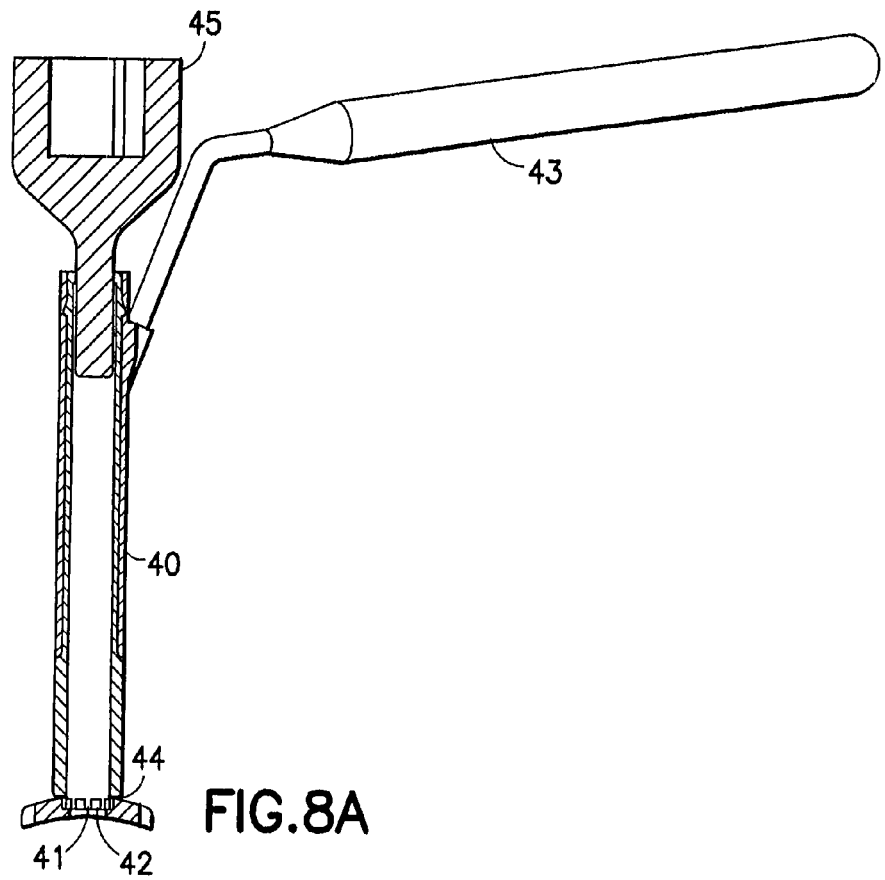
FIG. 8A is a cross-sectional view of a tool used in conjunction with the embodiment of FIG. 1.
Figure 8B:
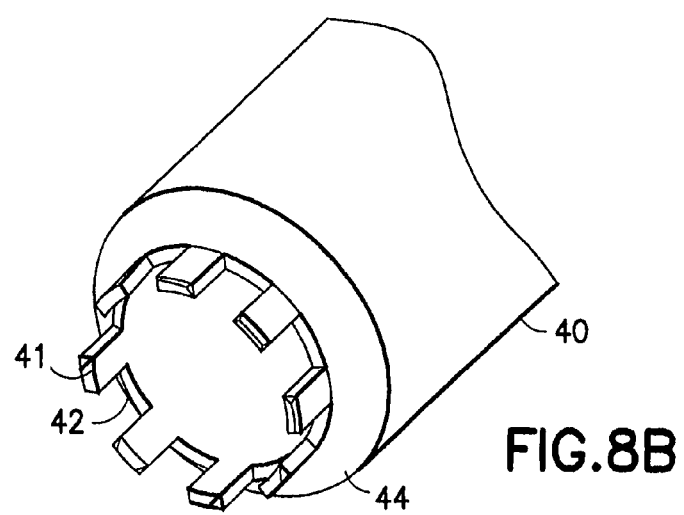
FIG. 8B is a perspective view of a portion of the tool of FIG. 8A.
Figure 9:
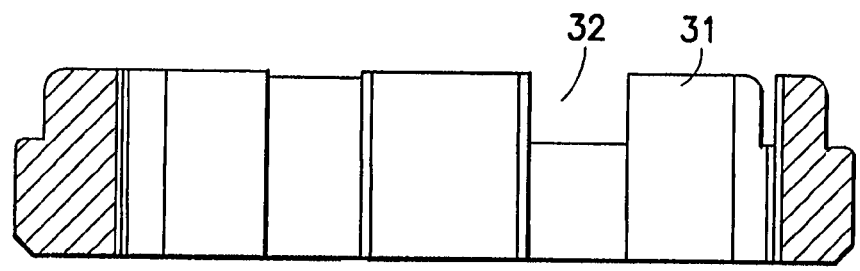
FIG. 9 is a cross sectional view of the washer of FIG. 7A.

Referring now generally to FIG. 3B, it is seen that each washer 18 is provided with a sidewall 28 (which sidewall 28 defines the aperture 19 though which the bone screw extends) and that the sidewall 28 has a varying thickness with respect to position along the washer's perimeter (see also, for example, FIG. 7A). In one embodiment, the washer 18 is provided with a first sidewall region 28a that is relatively thicker than a second sidewall region 28b (i.e., in this embodiment dimension "a" is greater than dimension "b" (see FIG. 3B)).

Figure 31:
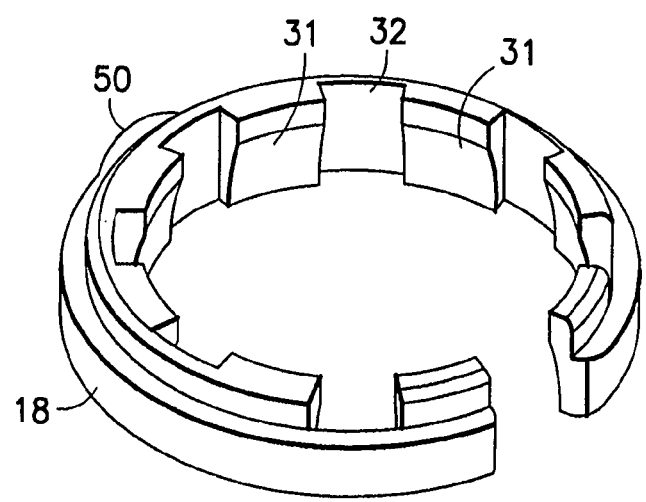
FIG. 31 depicts, in a perspective view, a split-ring washer according to another embodiment of the present invention.

Referring now to FIGS. 7A, 7B, 8A, 8B, 9 and 31, it is seen that in these examples (which examples are intended to be illustrative and not restrictive) the washer 18 may be provided with a series of splines 31 that are spaced at intervals around the inside perimeter of the washer (the washer of FIG. 31 is similar to the washers of FIGS. 7A, 7B, 8A, 8B and 9, with the exception that the washer of FIG. 31 is a split-ring washer). As depicted in the Figures, the splines may be solid members (which may extend from the perimeter of the washer towards the aperture 19 of the washer), and may be spaced apart by openings 32. The arrangement of the splines 31 and openings 32 may be complementary to a spline 41 and opening 42 arrangement provided on the head 44 of a tool 40 (see, e.g., FIGS. 8A and 8B). In operation, when the splines of the washer are engaged with the spaces of the tool, and vice versa, the application of a rotational force to the tool is translated to the washer, thereby turning the washer. The tool may, for example, be operated manually by handle 43, or by drill, in which case drill bit receiving channel 45 may be provided.

Referring once again to FIG. 7A, it is seen that in one example (which example is intended to be illustrative and not restrictive) the washer 18 may be provided with a detent 50 positioned on the outside of the sidewall 28. In this example, the sidewall of the bone plate may be provided with an indentation 52, which is sized to receive the detent 50 provided on the washer 18 (see, e.g., FIG. 10). When the bone plate and washer are assembled, the washer can be aligned so that the detent 50 resides in the indentation 52. This arrangement may inhibit unwanted rotation of the washer (e.g., until the time to actuate it, as described below).

Figure 6:
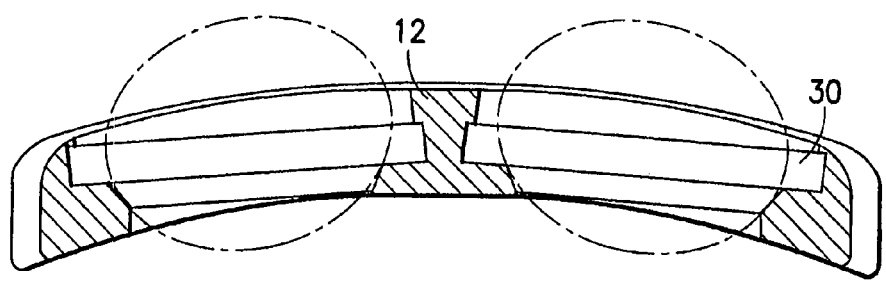
FIG. 6 is a cross sectional view of the bone plate of the embodiment of FIG. 1 (shown across the short side)

As seen in FIG. 6, bone plate 12 may be constructed with an arcuate shape. Of course, plates with other shapes and/or dimensions are possible.

In another example (which example is intended to be illustrative and not restrictive) bone plate 12 may be provided with one or more recesses 30, positioned within the bone plate 12 (see FIGS. 4A, 4B, 5 and 6). Each recess 30 may extend around the perimeter of each aperture 16 in the bone plate 12. Each recess 30 may be cut into the sidewall of the apertures in the bone plate 12. The lateral depth to which each recess 30 is cut may vary depending on the location on the perimeter of the recess 30. In one example (which example is intended to be illustrative and not restrictive), a first region 30a of the recess 30 may have a lateral depth that is greater than the lateral depth of a second region 30b of the recess 30 (i.e., in this embodiment dimension "a" is greater than dimension "b" (see FIG. 4B)). In another example (which example is intended to be illustrative and not restrictive), the lower portion of aperture 16 may be provided with a tapered sidewall 16a against which the bottom portion of the screw head 20 may rest (see FIG. 4B). The washer 18 may reside within the recess, aligned so that the first relatively thicker sidewall region 28a of the washer 18 is positioned within the first relatively deeper region 30a of the recess, and the second relatively thinner sidewall region 28b of the washer 18 is positioned in the second relatively shallower region 30b of the recess. In one embodiment, when the bone screw 14 is inserted into the aperture 16 of the bone plate 12, the washer 18 is substantially coplanar with the head 20 of the bone screw 14.

Figure 11:
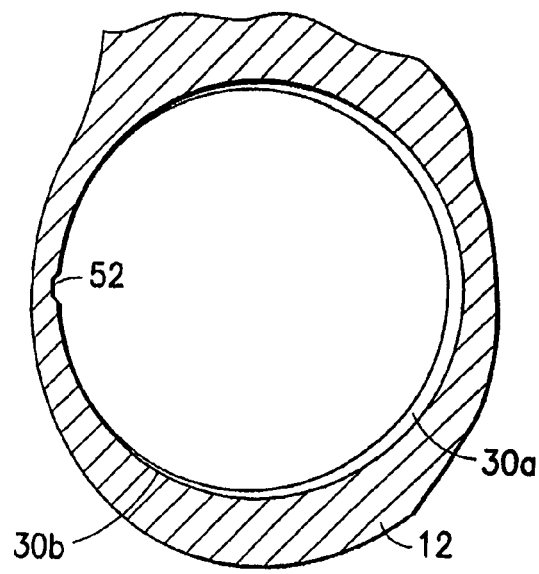
FIG. 11 is a partially sectioned view showing an the undercut or recess in connection with the embodiment of FIG. 1.

Referring now to FIG. 11, certain characteristics of the recess 30 as seen from the bottom of the bone plate 12 are shown. As shown here, the lateral depth of the second recess region 30b may be minimal (and may not be present at all) and a lateral depth may be provided essentially only in the first recess region 30a.

Figure 10:
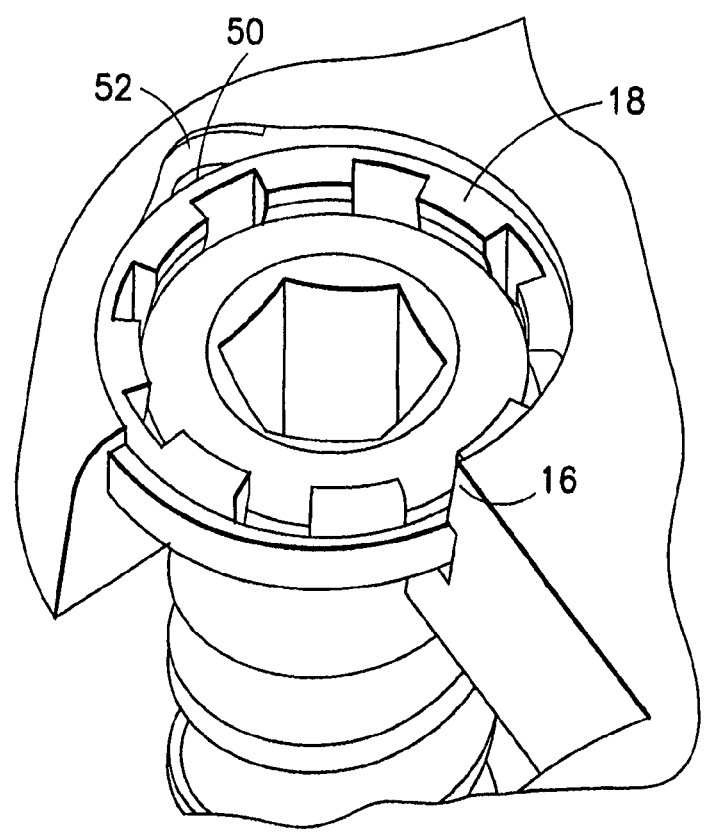
FIG. 10 is a partially sectioned perspective view of a portion of the embodiment of FIG. 1.
Figure 12A:
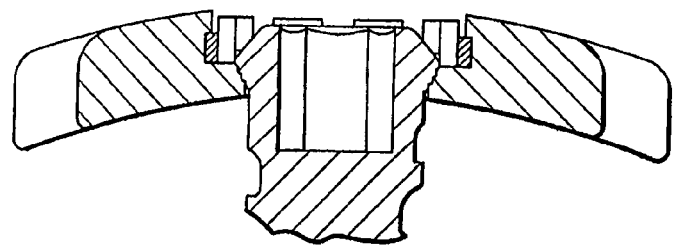
FIG. 12A depicts the washer of FIG. 7A in the open or unactuated position.
Figure 12B:
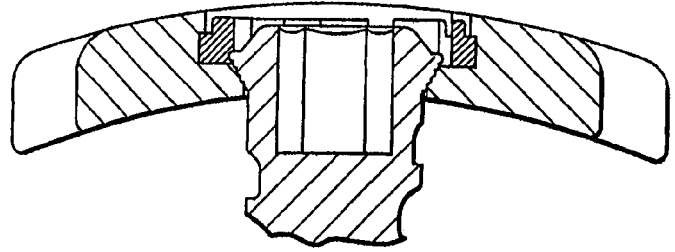
FIG. 12B depicts the washer of FIG. 7A in the closed or actuated position.

Referring now generally to FIGS. 12A and 12B, it is seen that when the bone plate assembly is implanted in a person, the bone plate is positioned over the bone, bones, and/or tissue to be joined by the bone plate 12. The bone screw(s) are inserted through the aperture(s) in the washer(s) (which washer(s) may reside in the recess(s) provided in the aperture(s) of the bone plate) and the bone screw(s) are installed in bone and/or tissue by known techniques. Each bone screw may be installed at a preselected angle, relative to the bone plate. In the position in which a washer is unlocked, the bone screw may pass through the opening in the washer (e.g., so that the bone screw may be installed at a preselected angle) (see FIG. 12A). To fix the bone screw (e.g., at the angle at which the bone screw is installed), the washer may be actuated by rotating the washer (e.g., with the tool, as described above). When the washer is rotated, the first relatively thicker sidewall region of the washer may move into the second relatively shallower region of the recess. Such movement may effectively cause the first relatively thicker sidewall region to extend laterally into the aperture in the bone plate (where the relatively thicker sidewall region impinges against the head of the bone screw, thereby applying a force thereto which wedges the bone screw between the washer and the opposite sidewall of the aperture) (see FIG. 12B). Such wedging of the bone screw may fix the bone screw at an angle (e.g., the angle at which the bone screw was inserted). FIGS. 10 and 12B depict the condition where the bone screw is wedged after actuating the washer.

In yet another embodiment of the present invention, depicted in FIGS. 13-21, another bone plate assembly is depicted. Shown here is a bone plate, bone screw, and a washer. With this arrangement, a bone plate that does not have a recess can be employed with this screw and washer pairing.

Figure 13:
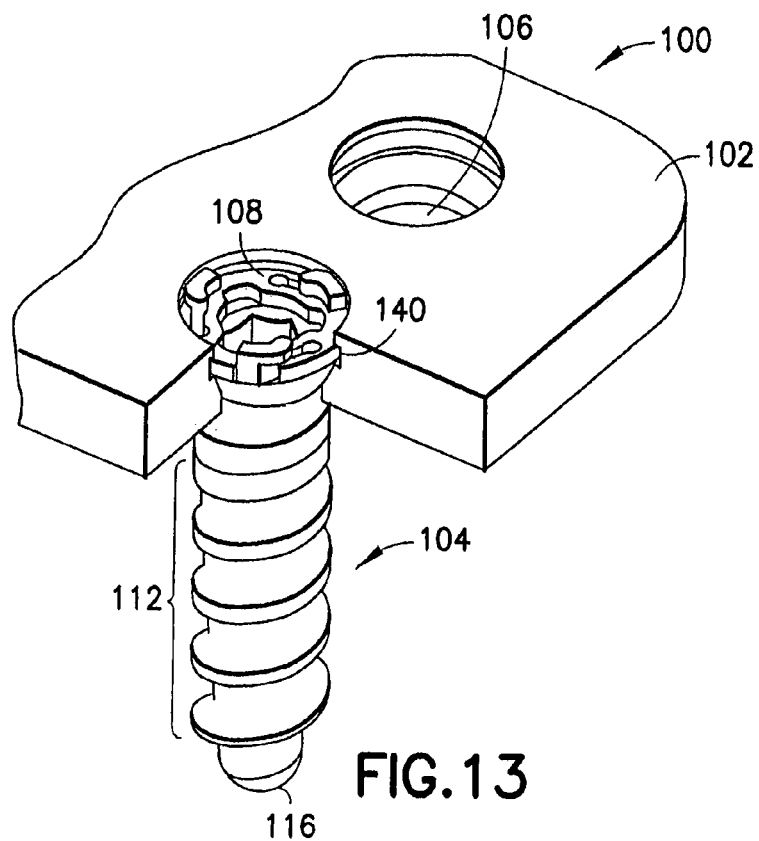
FIG. 13 is a partially sectioned perspective view of another embodiment of the present invention.

More particularly, FIG. 13 depicts a bone plate assembly 100, generally provided with bone plate 102, bone screw(s) 104 received in aperture(s) 106 in the bone plate 102, and washer(s) 108 that, alone or in conjunction with the bone plate 102, fix the bone screw(s) 104 in place (i.e., when the bone screw(s) 104 are inserted in the aperture(s) 106 in the bone plate 102). Each bone screw 104 has a head 110 sized so that it does not pass through the bone plate 102. Further, each bone screw 104 has a shank 112 provided with threads 114 (e.g., which threads 114 extend to tip 116). In one embodiment, the head 110 of each bone screw 104 may be provided with grooves 118 (see, e.g., FIGS. 4 and 5C). Bone plate assembly 100 is provided with washer(s) 108, each of which (as described below) is adapted to reside over a bone screw 104 and be joined therewith in a locking arrangement.

As shown in FIGS. 13 and 17-19, for example, in this embodiment the head 110 of bone screw 104 is provided with a number of tangs 120, spaced apart from each other, mounted on the upper surface of the head 110. The tangs 120 include wedges 122, which wedges 122 are not as wide as the upper portions of the tangs 120 (the wedges 122 are narrowed by an undercut). The head 110 is provided with an opening 107 in which a tool can be received to apply a rotational force, which rotational force permits the installation of the screw in tissue and/or bone.

Figure 14:
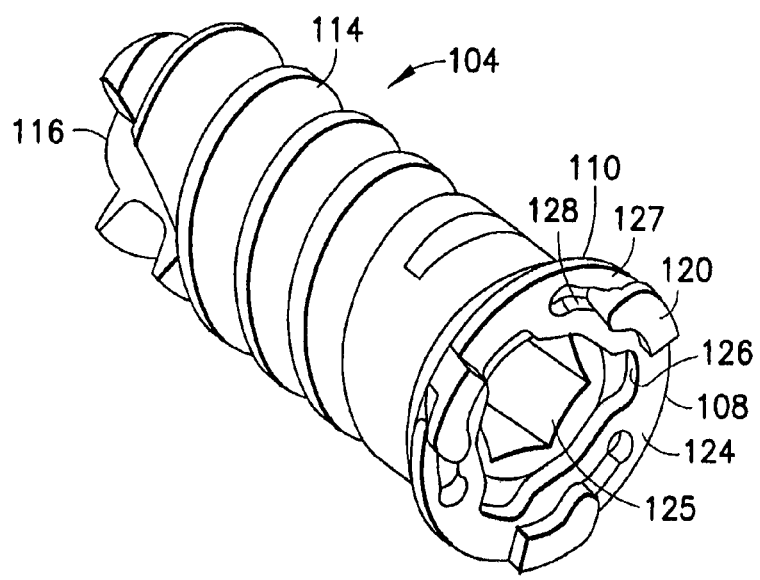
FIG. 14 is a perspective view of a washer and screw of the embodiment of FIG. 13.
Figure 15:
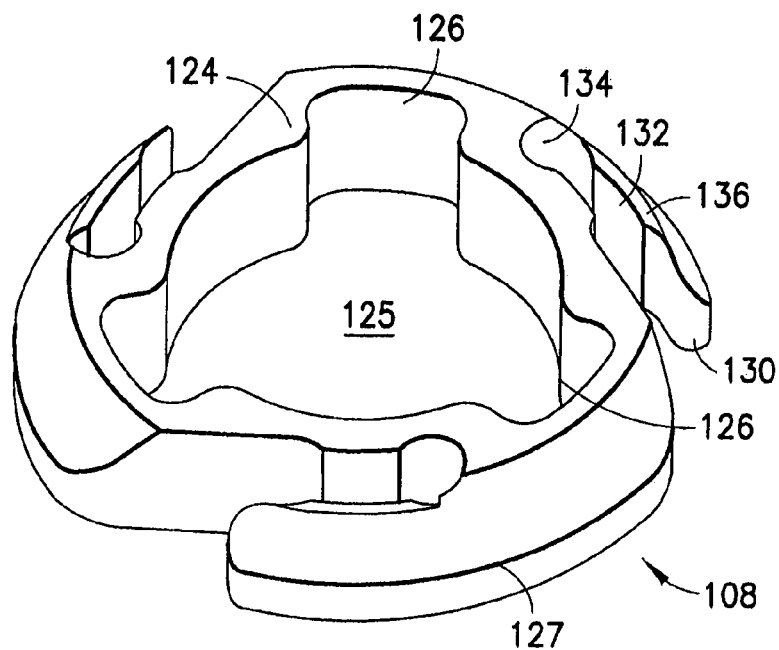
FIG. 15 is a perspective view of the washer of the embodiment of FIG. 13.
Figure 16:
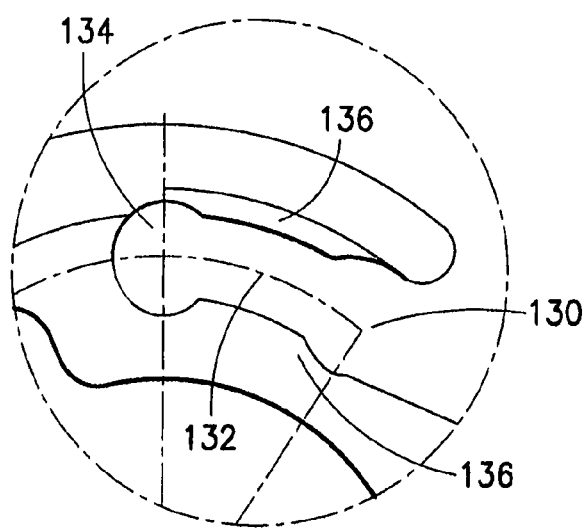
FIG. 16 is a top plan view showing in greater detail an aspect of the washer of the embodiment of FIG. 13.
Figure 17:
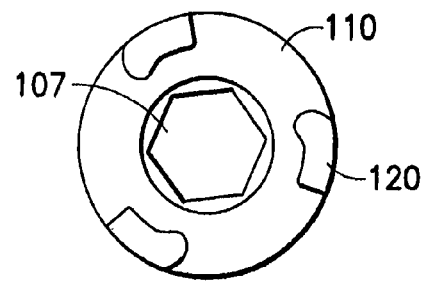
FIG. 17 is a top plan view of the screw of the embodiment of FIG. 13.
Figure 18:
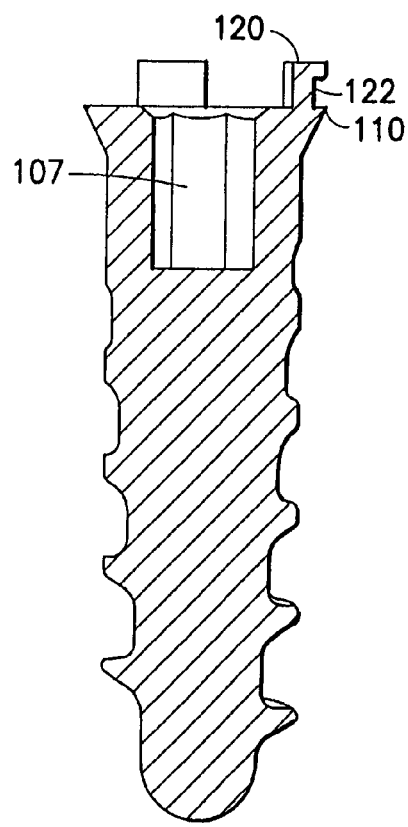
FIG. 18 is a side elevational view of the screw of the embodiment of FIG. 13.
Figure 19:
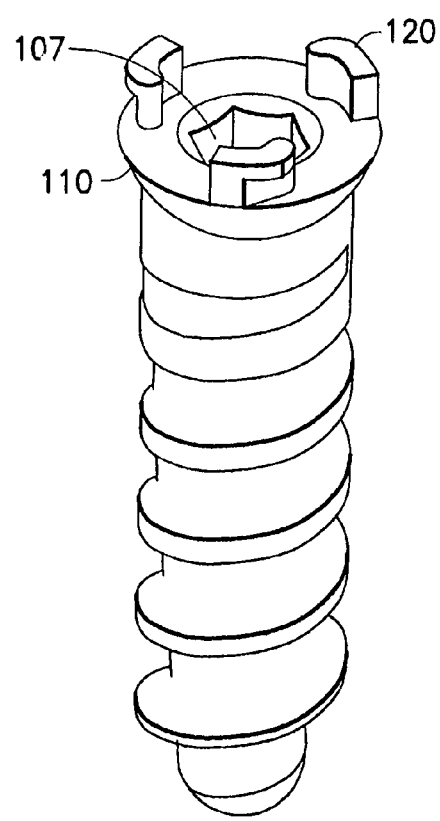
FIG. 19 is a perspective view of the screw of the embodiment of FIG. 13.
Figure 20:
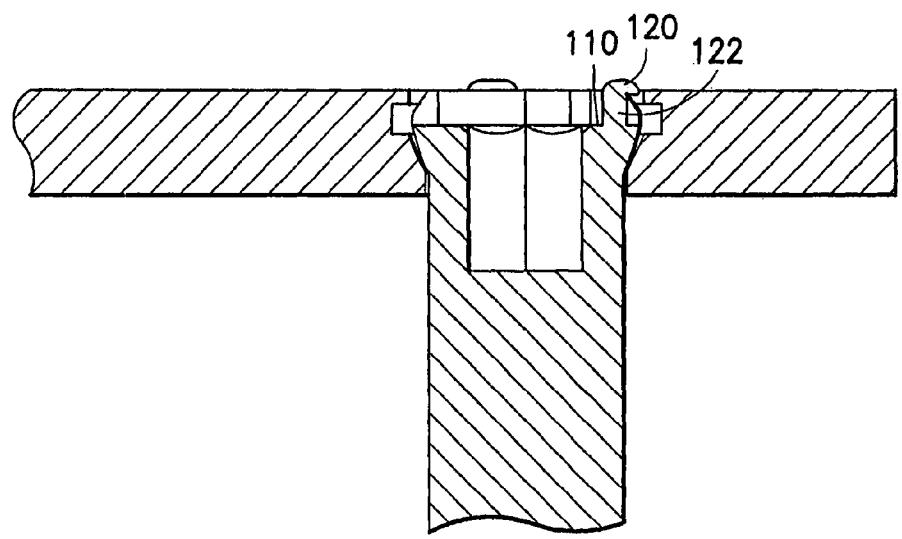
FIG. 20 is a cross sectional view of the washer and screw of the embodiment of FIG. 13.
Figure 21:
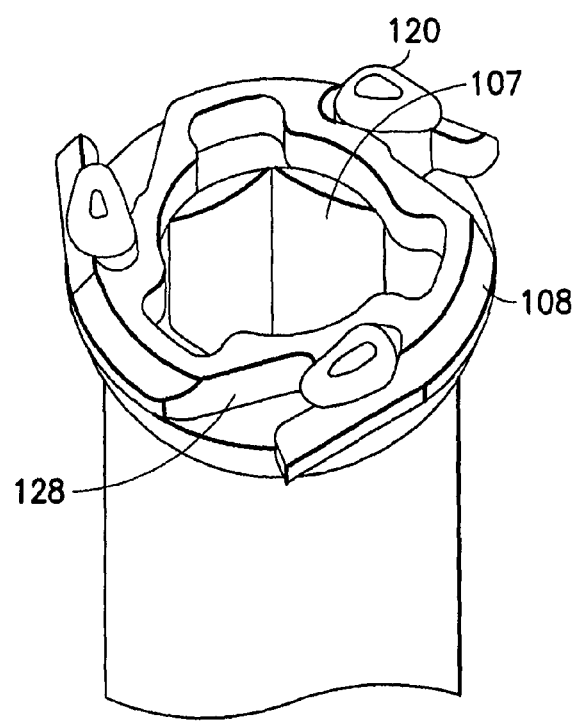
FIG. 21 is a perspective view of the embodiment of FIG. 13, where the washer has been opened.

Each washer 108 is sized and dimensioned to fit within one of the aperture(s) 106 in the bone plate 102. Each washer 108 is provided with a washer body 124 through which a central opening 125 is provided. A number of lobes 126 are provided on the periphery of the central opening 125. As depicted in the embodiment of FIG. 14, for example, three lobes are provided, though it should be understood that other arrangements are possible. Each washer 108 is also provided with splays 127, which are provided on the exterior of the washer 108. The splays 127 are separated from the remainder of the washer body 124 by tracks 128, which tracks 128 extend into the washer body 124. The tracks 128 are provided with an entrance portion 130, an intermediate track portion 132, and a terminus 134. The entrance portion 130 and the terminus 134 are wider than the intermediate track portion 132. The width of the intermediate track portion 132 is narrowed by the presence of nubs 136 that extend into the track (e.g., from the washer body 124 and/or the splays 128).

The washer 108 and the wedges 122/tangs 120 are designed to engage with each other in a locking arrangement. Relative to each other, the wedges 122 are slightly wider than the width of at least the intermediate track portion 132.

In operation, when the bone plate assembly is implanted in a person, the bone plate is positioned over the bone, bones, and/or tissue to be joined by/to the bone plate. The bone screw(s) are inserted through the aperture(s) in the bone plate and installed in bone and/or tissue by known techniques. Each bone screw may be installed at a preselected angle, relative to the bone plate. To fix the bone screw at a preselected angle (e.g., the angle at which the bone screw is installed), the washer is placed over the head of the bone screw, positioned so that the wedges 122 are poised to enter the track portions 128. A tool, provided with a head adapted to fit within the central washer opening 125 and lobes 126 is inserted into the washer, which is then rotated. The wedges 122 thereby enter the track portions 128. Since wedges 122 are wider than at least the intermediate track portions 132, the splays 127 are forced outward when the wedges enter the intermediate track portions 132 (see, e.g., FIG. 21). The splays are forced into an abutting arrangement with the sidewalls of the aperture in which the bone screw 106 and washer reside 108. The abutting arrangement between the splays 127 and the sidewalls of the bone plate 102 fixes the bone screw 104 (e.g., at the angle at which the bone screw 104 was installed).

In another example (which example is intended to be illustrative and not restrictive) the splays 127 may enter an undercut 140 in the aperture(s) 106 (see, e.g., FIG. 13).

Figure 29:
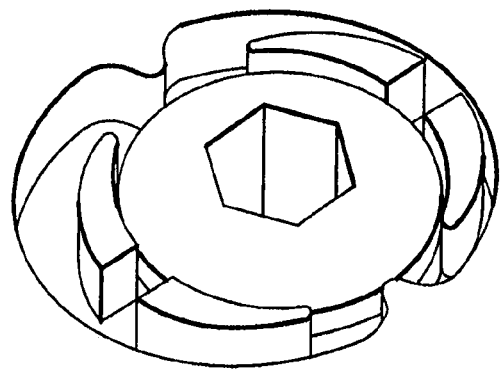
FIG. 29 depicts, in a perspective view, another embodiment in which a double lobed washer is employed.
Figure 30:
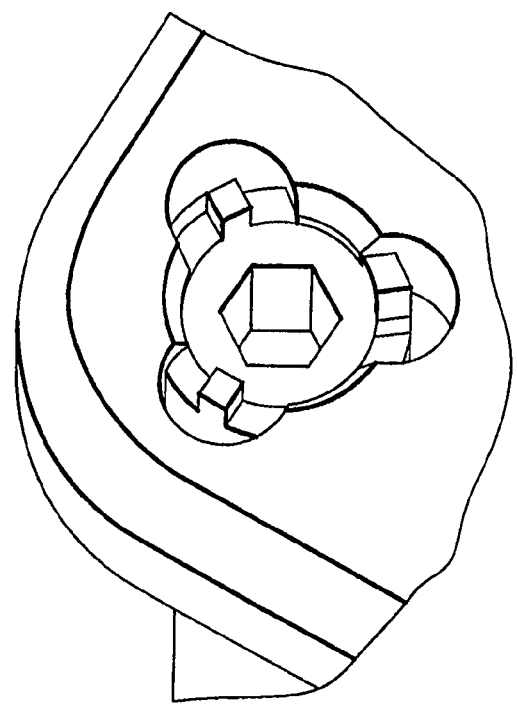
FIG. 30 depicts, in a perspective view, another embodiment in which a tri-lobed washer is employed.

In another embodiment FIG. 29 depicts, in a perspective view, a double lobed washer. The double lobed washer may be shaped differently than the recess and/or aperture in the bone plate which received the washer. When the washer is rotated, it is deformed, compressing it against the bone screw, fixing the angle of the bone screw (e.g., the angle at which the bone screw is inserted). The embodiment of FIG. 30 is similar. FIG. 30 depicts, in a perspective view, a tri-lobed washer. Again, the tri-lobed washer may be shaped differently than the recess and/or aperture in the bone plate. When the washer is rotated, it is deformed, compressing it against the bone screw and fixing the angle of the bone screw (e.g., the angle at which the bone screw is inserted). The embodiments of FIGS. 29 and 30 may thus operate without a recess.

Figure 22A:
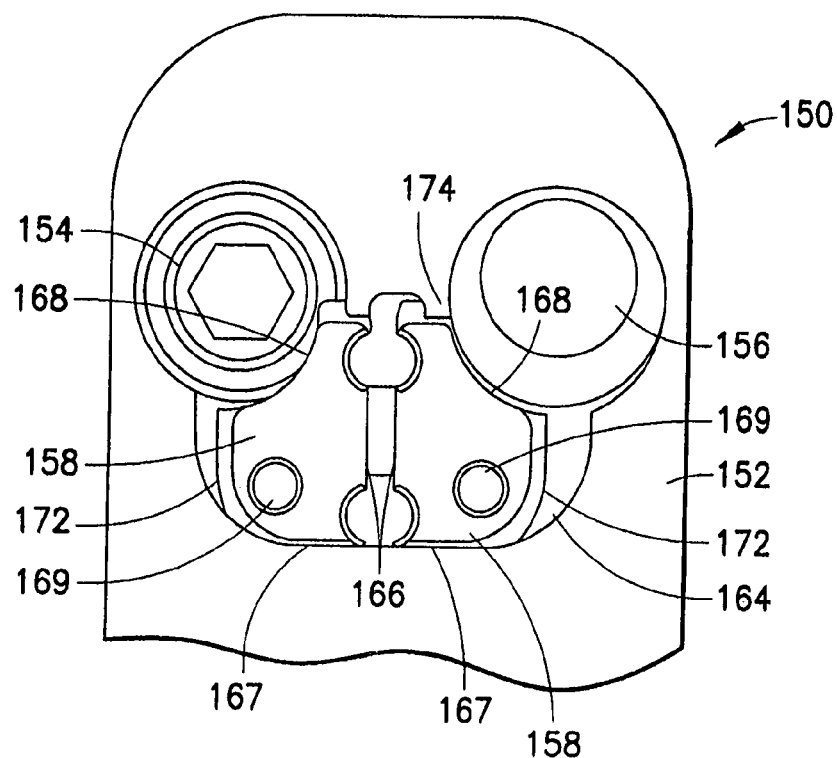
FIG. 22A is a top plan view of another embodiment of the present invention.
Figure 22B:
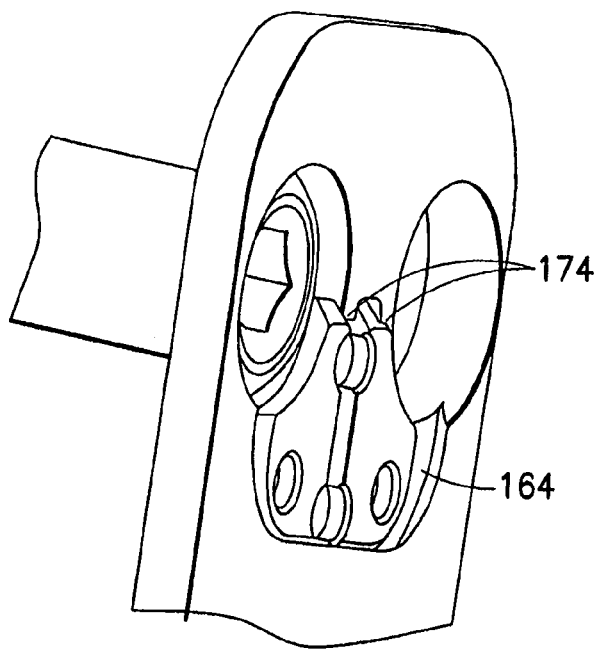
FIG. 22B is a perspective view of the embodiment of FIG. 22A.
Figure 22C:
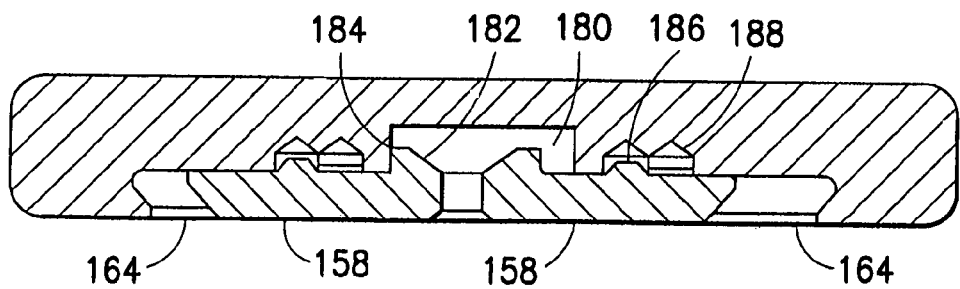
FIG. 22C is cross sectional view of the embodiment of FIG. 22A.
Figure 23:
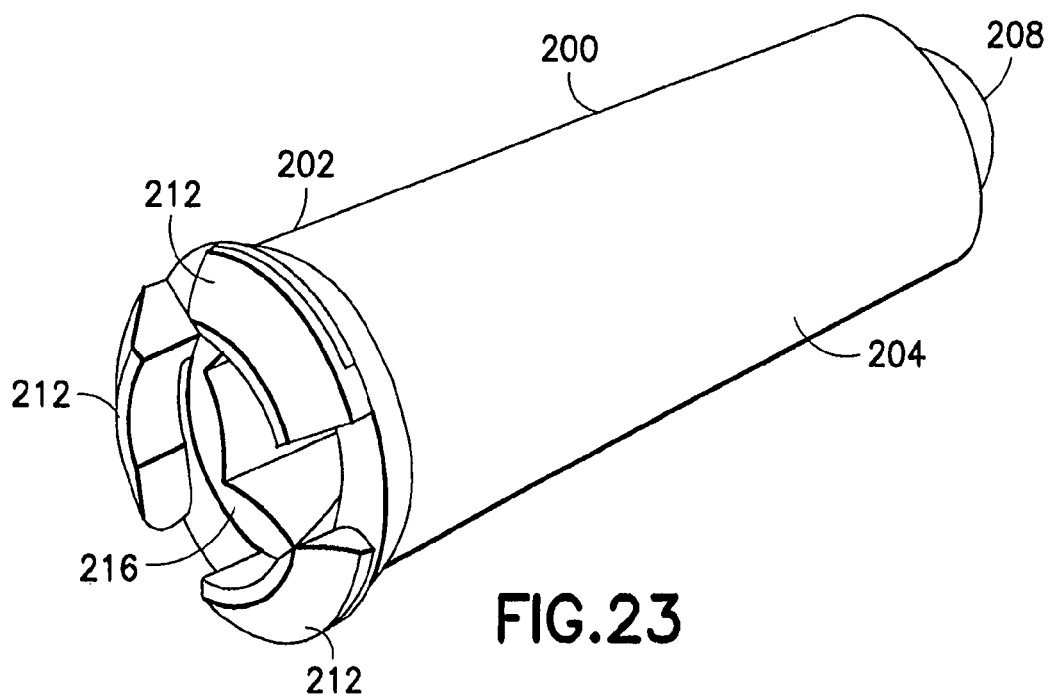
FIG. 23 is a perspective view of another embodiment of the present invention.
Figure 24:
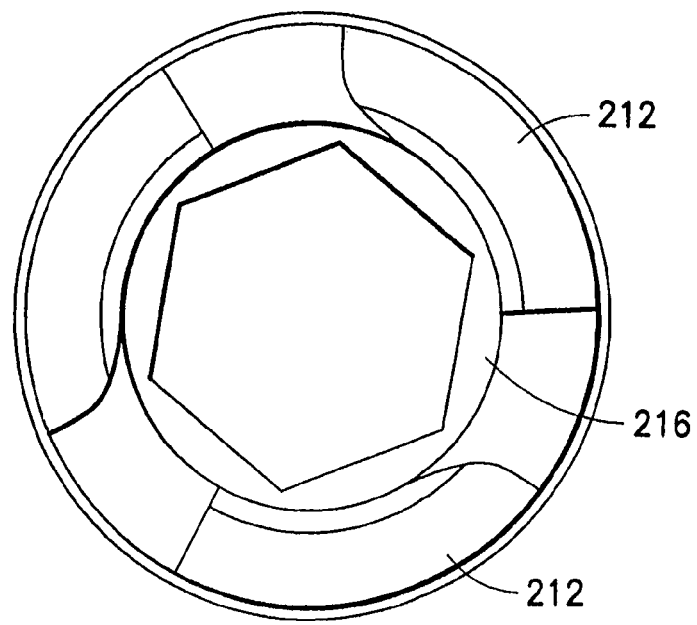
FIG. 24 is top plan view of the embodiment of FIG. 23.
Figure 25:
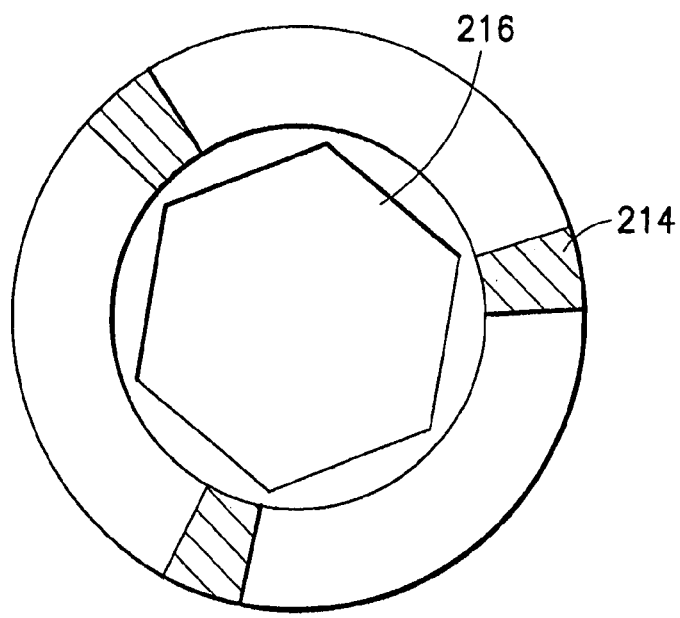
FIG. 25 is a cross sectional view of the embodiment of FIG. 23.
Figure 26:
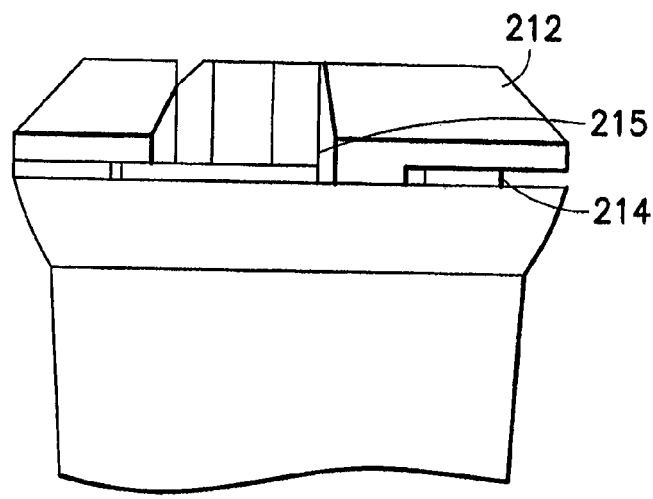
FIG. 26 is a side elevational view of the embodiment of FIG. 23.
Figure 27:
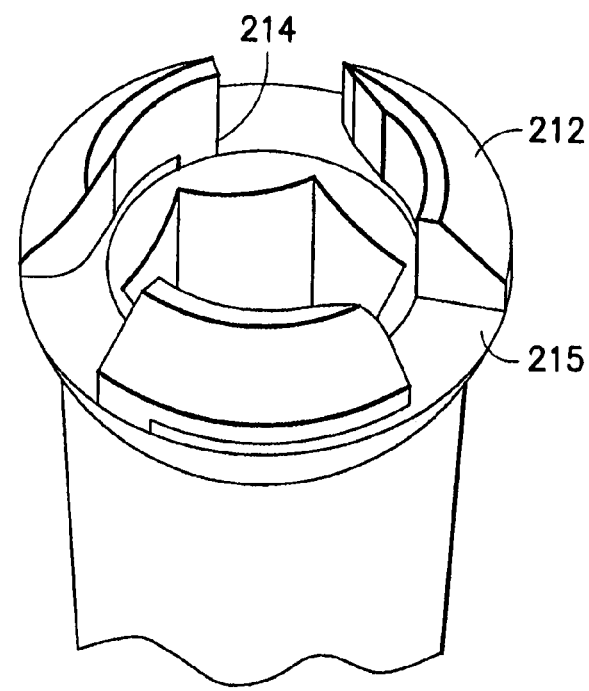
FIG. 27 is a perspective view of the embodiment of FIG. 23.

In another embodiment, shown in FIGS. 22A, 22B and 22C, there is shown a bone plate assembly 150, generally provided with bone plate 152, bone screw(s) 154 (which bone screw(s) 154 are received in aperture(s) 156 in the bone plate 152), and moveable doors 158 (which moveable doors 158 may slide and may fix the bone screw(s) 154 in place when the bone screw(s) 154 are inserted in the aperture(s) 156 in the bone plate 152). Each bone screw 154 has a head sized so that the head does not pass through the bone plate 152. Further, each bone screw 154 has a shank provided with threads that extend to a tip. In one example (which example is intended to be illustrative and not restrictive), the head of the bone screw may be provided with grooves. Bone plate assembly 150 is provided with cut out portion(s) 164, on an upper surface of the bone plate assembly 150, to which the moving doors 158 are slidably mounted. The cut out portion(s) 164 are positioned adjacent the aperture(s) 156, at a segment of the edge thereof.

In one example (which example is intended to be illustrative and not restrictive), each moveable door 158 is provided with two substantially flat sides 166, 167, cutouts of partial circles 168, full cut out circle 169, and arcuate side 172. It should be apparent that other dimensional arrangements are possible. The moveable doors 158 are positioned in the cut out portion(s) 164 on the upper surfaced of the bone plate 152, and are retained therein by lip 174 provided at the upper sidewall of the cut out portion 164. Dovetail undercuts may also be present along other upper sidewalls to maintain the doors in place. The cut out portion(s) 164 are sized slightly greater than the moveable doors. Thus, when each bone screw is positioned in an aperture 156 of the bone plate 152, the moveable door 158 can be slid in the direction of the aperture 156, in order to cover the bone screw 154 (and thus fix the bone screw 154 in place).

Referring now to FIG. 22C, in one example (which example is intended to be illustrative and not restrictive) a channel 180 is fully or partially bored into the bone plate 152 at a location between the cut out portions(s) 164. Still referring to FIG. 22C, in another example (which example is intended to be illustrative and not restrictive) the moveable doors 158 are provided with stops 182 that depend from the doors, into the channel 180. When the door is moved into the locked position, as shown in the left hand side of FIG. 22C, the stop engages channel sidewall 184, inhibiting further movement of the door. Detents 186 and indentations 188 may also be used if desired.

Another embodiment of the present invention is depicted in FIGS. 23-27. In this embodiment a bone screw 200 is provided with a head 202 sized so that it does not pass through a bone plate (not shown) and shank 204 provided with threads (not shown) that extend to tip 208. In one example (which example is intended to be illustrative and not restrictive), the head 202 of the bone screw 200 may be provided with grooves (not shown).

As seen in these Figures, the head 202 of bone screw 200 is provided with a number of splays 212, spaced apart from each other, and extending around the periphery of the head of the bone screw 200. The splays 212 are mounted on the upper surface of the head 202, and in one example (which example is intended to be illustrative and not restrictive), may have an arcuate shape. Each splay 212 extends around a portion of the periphery of the head of the bone screw 200. Each splay 212 is mounted upon a wedge 214, (wherein the wedges 214 extend up from the head of the screw). The wedges 214 join the splay 212 at the base of the splay 212, elevating the splay 212 off of the head of the bone screw 200. Spaces 215 are present between the portions of the splay 212, which extend over the periphery of the head of the bone screw 200, and the head of the bone screw 200 itself.

In this embodiment, after the bone screw 200 has been inserted into an aperture in a bone plate, and installed at a preselected angle, the angle can be fixed by forcing the splays outward (i.e., into a locking and abutting arrangement with the sidewalls of the aperture in the bone plate). In operation, a tool is inserted into the interior space 216 and rotated (to force the splays outward, into an abutting and locking arrangement with the sidewalls of the apertures).

Figure 28:
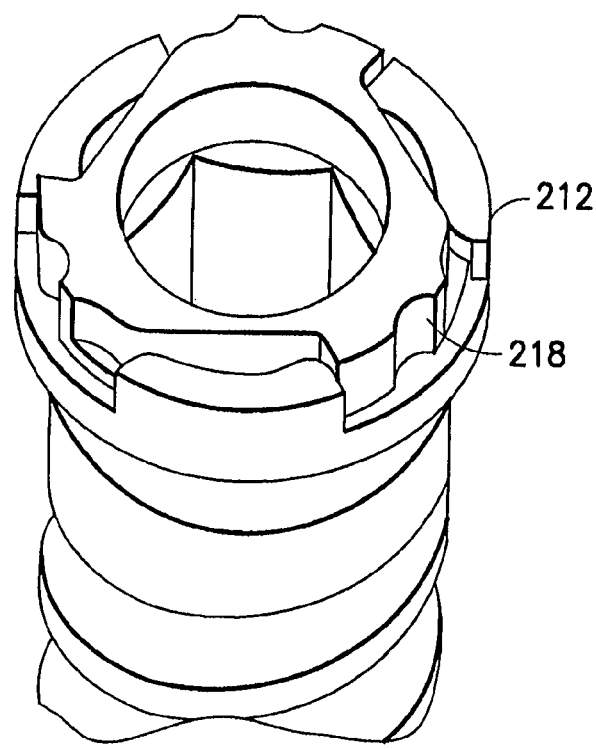
FIG. 28 depicts another embodiment of the present invention.

In another embodiment, shown in FIG. 28, a cam 218 may be utilized. In one example (which example is intended to be illustrative and not restrictive), the cam may be rotatably mounted to the head 202 of the bone screw 200. In operation, the splays are forced outward, by rotating the cam 218 (which cam 218 moves against the interior walls of the splays). Here, the cam 218 provides a counterforce against the force applied by the sidewalls of the apertures (which counterforce facilitates the maintaining of the splays 212 in a locking and abutting arrangement with the sidewalls of the aperture in the bone plate).

In another embodiment one or more of the washers may be a split-ring washer.

While a number of embodiments of the present invention have been described, it is understood that these embodiments are illustrative only, and not restrictive, and that many modifications may become apparent to those of ordinary skill in the art.

What is claimed is:

1. An implant assembly adapted to be fixed to a bone using at least one bone screw having a thinner region and a thicker region, the implant assembly comprising:
   an implant member, wherein the implant member has an aperture extending through the implant member, wherein the aperture includes a first region sized to permit the thinner region of the bone screw but not the thicker region of the bone screw to pass through and the aperture includes a second region sized to permit both the thinner region of the bone screw and the thicker region of the bone screw to pass through;
   a first interior perimeter surface in the implant member defined by the first region of the aperture;
   a second interior perimeter surface in the implant member defined by the second region of the aperture; and
   a washer disposed within the aperture in the second region thereof, wherein the washer has a hole, the hole having a longitudinal axis and being large enough to permit both the thinner region of the bone screw and the thicker region of the bone screw to pass through, wherein the washer has at least a first sidewall region with a first wall thickness and a second sidewall region with a second wall thickness, the first and second wall thicknesses being defined in a plane normal to the longitudinal axis of the hole, wherein the first wall thickness is greater than the second wall thickness;
   wherein, when the bone screw is inserted in the aperture of the implant member and the hole of the washer such that the thicker region of the bone screw is in the second region of the aperture, rotation of the washer causes movement of the first region of the washer relative to the second interior perimeter surface such that the washer applies force to the bone screw to press the bone screw against the implant member and to fix the bone screw in orientation relative to the implant member.

2. The implant assembly of claim 1, wherein the second interior perimeter surface includes a recess in at least a portion thereof, and at least a portion of the washer enters the recess.

3. The implant assembly of claim 2, wherein the recess includes at least a first region and a second region, and wherein the recess is shallower in the first region than in the second region.

4. The implant assembly of claim 3, wherein, when the bone screw is inserted in the aperture of the implant member and the hole of the washer such that the thicker region of the bone screw is in the second region of the aperture, rotation of the washer causes movement of the first region of the washer from the first region of the recess to the second region of the recess such that the washer applies force to the bone screw to press the bone screw against the implant member and to fix the bone screw in orientation relative to the implant member.

5. The implant assembly of claim 1, wherein the washer applies force to the bone screw to press the bone screw against the first interior perimeter surface.

6. The implant assembly of claim 5, wherein the bone screw includes grooves, at least a portion of which grooves are brought into contact with the first interior perimeter surface when the washer applies force to the bone screw to press the bone screw against the first interior perimeter surface.

7. The implant assembly of claim 5, wherein the first region of the aperture is shaped such that the first interior perimeter surface provides two lines of contact with the bone screw as the bone screw is pressed against the first interior perimeter surface by the washer.

8. The implant assembly of claim 1, further comprising a detent disposed on the washer, wherein the detent engages the second interior perimeter surface to provide sufficient friction to prohibit the washer from rotating due to contact with the bone screw as the bone screw is screwed into the bone.

9. The implant assembly of claim 8, further comprising an indentation in the second interior perimeter surface, wherein the detent engages the indentation to provide sufficient friction to prohibit the washer from rotating due to contact with the bone screw as the bone screw is screwed into the bone.

10. The implant assembly of claim 1, wherein the implant member has a top surface and a bottom surface, wherein the first region of the aperture is adjacent the bottom surface of the implant member, and wherein the second region of the aperture is adjacent the top surface of the implant member.

11. The implant assembly of claim 10, wherein the first region of the aperture tapers from wider to narrower in a direction moving from the top surface of the implant member towards the bottom surface of the implant member.

12. The implant assembly of claim 11, wherein the bone screw is inserted from the top surface of the implant member towards the bottom surface of the implant member.

13. The implant assembly of claim 10, wherein the bottom surface of the implant member is contoured to substantially match a contour of the bone to which the implant member is affixed.

14. The implant assembly of claim 1, wherein the implant assembly is used for performing at least one of: (a) fusing at least two bones; and (b) healing a fracture in a bone.

15. The implant assembly of claim 1, wherein the thinner region of the bone screw includes a threaded shank and the thicker region of the bone screw includes a head.

16. The implant assembly of claim 15, wherein the head of the bone screw includes a mechanism for engaging a driving tool.

17. The implant assembly of claim 16, wherein the mechanism for engaging the driving tool is a hex socket.

18. The implant assembly of claim 1, wherein the washer includes a mechanism for engaging a driving tool.

19. The implant assembly of claim 18, wherein the mechanism for engaging the driving tool is a spline.

20. The implant assembly of claim 1, wherein the washer is a split-ring washer.

21. An implant assembly adapted to be fixed to a bone using at least two bone screws, each of the bone screws having a thinner region and a thicker region, the implant assembly comprising:
  an implant member, wherein the implant member has a top surface and a bottom surface and wherein the implant member has at least two apertures extending therethrough, wherein each aperture includes a lower region sized to permit the thinner region of one of the bone screws but not the thicker region of one of the bone screws to pass through, wherein each aperture includes an upper region sized to permit both the thinner region of one of the bone screws and the thicker region of one of the bone screws to pass through, and wherein the lower region of the aperture is adjacent the bottom surface of the implant member and the upper region of the aperture is adjacent the top surface of the implant member;
  at least two lower interior perimeter surfaces in the implant member, each of the lower interior perimeter surfaces is defined by the lower region of a respective one of the apertures;
  at least two upper interior perimeter surfaces in the implant member, each of the upper interior perimeter surfaces is defined by the upper region of a respective one of the apertures; and
  at least two washers, each of the washers is disposed within the upper region of a respective one of the apertures, wherein each washer has a hole, the hole having a longitudinal axis and being large enough to permit both the thinner region of one of the bone screws and the thicker region of one of the bone screws to pass through, wherein each washer has at least a first sidewall region with a first wall thickness and a second sidewall region with a second wall thickness, the first and second wall thicknesses being defined in a plane normal to the longitudinal axis of the hole, and wherein the first wall thickness is greater than the second wall thickness;
  wherein each upper interior perimeter surface includes a recess in at least a portion thereof;
  wherein at least a portion of each washer enters a respective one of the recesses;
  wherein each recess includes at least a first region and a second region such that each recess is shallower in the first region than in the second region; and
  wherein, when each of the bone screws is inserted in a respective aperture of the implant member and a hole of a respective one of the washers such that the thicker region of the bone screw is in the upper region of the aperture, rotation of the washer causes movement of the first region of the washer from the first region of the respective recess to the second region of the recess such that the washer applies force to the bone screw to press the bone screw against the implant member and to fix the bone screw in orientation relative to the implant member.

22. The implant assembly of claim 21, wherein each recess defines an interface surface between the upper interior perimeter surface and the lower interior perimeter surface and each washer applies force to a respective bone screw to press the bone screw against at least one of a respective lower interior perimeter surface and a respective interface surface.

23. The implant assembly of claim 22, wherein each bone screw includes grooves, at least a portion of which grooves are brought into contact with at least one of a respective lower interior perimeter surface and a respective interface surface when each washer applies force to a respective bone screw to press the bone screw against at least one of a respective lower interior perimeter surface and a respective interface surface.

24. The implant assembly of claim 22, wherein the lower region of each aperture is shaped such that the lower interior perimeter surface provides two lines of contact with a respective bone screw as a respective bone screw is pressed against the lower interior perimeter surface by a respective washer.

25. The implant assembly of claim 21, further comprising a detent disposed on each of the washers, wherein each detent engages a respective upper interior perimeter surface to provide sufficient friction to prohibit each washer from rotating due to contact with a respective bone screw as the bone screw is screwed, into the bone.

26. The implant assembly of claim 25, further comprising an indentation in each of the second interior perimeter surfaces, wherein a respective detent engages a respective indentation to provide sufficient friction to prohibit each washer from rotating due to contact with a respective bone screw as the bone screw is screwed into the bone.

27. The implant assembly of claim 21, wherein the lower region of each aperture tapers from wider to narrower in a direction moving from the top surface of the implant member towards the bottom surface of the implant member.

28. The implant assembly of claim 27, wherein each bone screw is inserted from the top surface of the implant member towards the bottom surface of the implant member.

29. The implant assembly of claim 21, wherein the bottom surface of the implant member is contoured to substantially match a contour of the bone to which the implant member is affixed.

30. The implant assembly of claim 21, wherein the implant assembly is used for performing at least one of: (a) fusing at least two bones; and (b) healing a fracture in a bone.

31. The implant assembly of claim 21, wherein the thinner region of each bone screw includes a threaded shank and the thicker region of each bone screw includes a head.

32. The implant assembly of claim 31, wherein the head of each bone screw includes a mechanism for engaging a driving tool.

33. The implant assembly of claim 32, wherein the mechanism for engaging the driving tool is a hex socket.

34. The implant assembly of claim 21, wherein each washer includes a mechanism for engaging a driving tool.

35. The implant assembly of claim 34, wherein the mechanism for engaging the driving tool is a spline.

36. The implant assembly of claim 21, wherein the implant member includes between 2 and 8 apertures.

37. The implant assembly of claim 36, wherein the implant assembly includes the same number of washers as apertures.

38. The implant assembly of claim 21, wherein at least one of the washers is a split-ring washer.

* * * * *